(12) United States Patent
Voss

(10) Patent No.: US 6,177,125 B1
(45) Date of Patent: *Jan. 23, 2001

(54) METHOD OF PRODUCING COATED TABLETS

(76) Inventor: Gunter M. Voss, Ziegelstadel 10, Diessen/Ammersee D-86911 (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/793,592

(22) PCT Filed: Aug. 3, 1995

(86) PCT No.: PCT/DE95/01012

§ 371 Date: Apr. 29, 1997

§ 102(e) Date: Apr. 29, 1997

(87) PCT Pub. No.: WO96/04128

PCT Pub. Date: Feb. 15, 1996

(30) Foreign Application Priority Data

Aug. 3, 1994 (DE) .................................. 44 27 390
Oct. 20, 1994 (DE) .................................. 44 37 442

(51) Int. Cl.⁷ ..................................... A61J 3/10
(52) U.S. Cl. ................... 427/2.14; 264/319; 264/240; 264/241
(58) Field of Search .............. 427/2.14, 2.21, 427/2.22; 264/229, 319, 240, 241, 271.1

(56) References Cited

U.S. PATENT DOCUMENTS

| | | | |
|---|---|---|---|
| 4,127,650 | * 11/1978 | Buehler | 424/184 |
| 4,198,390 | * 4/1980 | Rider | 424/21 |
| 4,347,235 | * 8/1982 | Daunora | 424/44 |
| 4,497,158 | * 2/1985 | Durr et al. | 53/428 |
| 4,880,636 | * 11/1989 | Franz | 424/480 |
| 5,073,384 | * 12/1991 | Valentine et al. | 424/474 |
| 5,178,874 | * 1/1993 | Kwan et al. | 424/438 |
| 5,322,655 | * 6/1994 | Ebey | 264/40.5 |
| 5,350,548 | * 9/1994 | Hinzpeter et al. | 264/113 |
| 5,460,827 | * 10/1995 | Sanderson et al. | 264/113 |
| 5,480,654 | * 1/1996 | Tanaka et al. | 427/2.21 |
| 5,569,484 | * 10/1996 | Muller et al. | 427/2.14 |
| 5,599,577 | * 2/1997 | Stevens et al. | 427/2.14 |

FOREIGN PATENT DOCUMENTS

| | | |
|---|---|---|
| 1 025 569 | 3/1958 | (DE) . |
| 0 349 777 A1 | 1/1990 | (EP) . |
| 0 590 963 A1 | 4/1994 | (EP) . |

* cited by examiner

*Primary Examiner*—Shrive Beck
*Assistant Examiner*—Jennifer Kolb
(74) *Attorney, Agent, or Firm*—Staas & Halsey LLP

(57) ABSTRACT

A method is described for manufacturing coated tablets made of tablet cores and coating granulate using a press that has at least one compression chamber with preferably an upper and a lower punch and a feeding device for tablet cores.

The method according to the invention is characterized by the fact that before the coating granulate is compressed, at least one pasty tablet core is added to the coating granulate to be compressed and in that the coating granulate and tablet core(s) are compressed in a single compression step.

21 Claims, No Drawings

METHOD OF PRODUCING COATED TABLETS

BACKGROUND OF THE INVENTION

1. Technical Field

The invention relates to a method for manufacturing coated tablets from tablet cores and coating granulate using a press that has at least one compression chamber, preferably with an upper and a lower punch and a feeding device for tablet cores.

2. Description of the Related Art

Methods according to the related art are based as a rule on so-called rotary tablet machines with a high processing speed.

The manufacture of coated tablets has thus far been performed in two steps:

In the first manufacturing step the future cores of the coated tablets are compressed and in the second step the tabletting material for the lower half of the coating is precompressed, the core is placed on the precompressed bed, and is then compressed to form a coated tablet after tabletting material for the upper half of the coating has been added to the die.

The first manufacturing step can be further differentiated into a loading phase in which the tabletting material is added to the die cavity, a compression phase, and an ejection phase in which the finished tablet is removed from the die with the aid of a lower punch.

The second manufacturing step conventionally consists of a first filling phase in which the tabletting material for the lower half of the coated tablet to be produced is loaded into the die, a precompression phase in which the tabletting material that has been added is precompressed slightly so that the core to be added can be placed, a metering phase in which the core is added to the precompressed bed, a second filling phase in which the upper half of the coating is loaded into the die, a compression phase to compress the coated tablet, and an ejection phase that serves to remove the compressed tablet from the die with the aid of the lower punch.

DESCRIPTION OF THE INVENTION

The invention has as its goal the provision of a method for manufacturing coated tablets that simplifies the manufacture of coated tablets and in which in particular only a single manufacturing step is required for.

According to the invention, the cores do not consist of tablet cores previously manufactured in a separate compression process which are added as solidified masses to the tabletting material, but instead consist of a pasty preparation of the contents in a dispersing agent, such as alcohol or Miglyol™ for example. This makes it possible to add at least one pasty tablet core to the coating granulate to be compressed before compressing the coating granulate. Then the coating granulate is compressed along with the tablet core in a single compression step.

In particular, the method according to the invention makes it possible to add at least two tablet cores, separated from one another, to the tablet in such fashion that the surrounding granulate prevents the respective contents of the tablet cores from engaging in chemical or physical reactions with one another. For this purpose, contents can be provided in a tablet that would enter into undesired reactions if they were processed together.

The pasty tablet core or cores can be added in many different ways. However, preferably, the pasty tablet core mass has a consistency and especially a viscosity such that the tablet core mass is injected by means of a high-pressure feed shoe into the coating granulate.

However, the following problem occurs when the tablet core or cores are added:

By combining the two manufacturing steps, separate in the prior art, into a single manufacturing step, the metering and division of the tablet cores, which is accomplished in the prior art by separate compression of the tablet cores, must take place during the addition of the tablet core masses to the tabletting material of the tablet coating. As a result, the pasty tablet core mass must be divided into portions whose volumes must be metered precisely.

For this reason, in a preferred embodiment of the invention a metering device is provided that must meet the technical demands of maximally precise mass flow metering. This metering device consists of a Proportional valve.

The high metering accuracy of the tabletting core mass that is achieved in compressed tablet cores by the parameters that are conventional in tablet manufacture (volume of die cavity, density of tabletting material) and control values (press pressure, compressive strength), at the high processing rates that rotary tablet machines in particular can achieve (60,000 tablets or more per hour), is achieved by a piezoelectric proportional valve that operates in proportion to the control and which by adjusting the through flow volume and cross section, permits precise direct injection of the highly concentrated mass into the tabletting material, which would not be possible with conventional valves. This piezoelectric proportional valve is preferably controlled by a computer or an electronic control unit. In addition, sensors for pressure, temperature, etc. can be provided whose output signals are fed to the control computer for the proportional valve or valves.

The proportional valve used according to the invention can produce pressures from 30 to 50 bars and frequencies of 4 kHz, with one manufacturing step lasting 50 microseconds.

Another improvement on the method according to the invention relates to the compression chamber which is initially partially filled with coating granulate, then the pasty tablet core or cores are added, and the press chamber is filled completely with coating granulate. The coating granulate added to the compression chamber can be precompressed before the tablet core or cores are added.

This improvement has the particular advantage that after precompression, a film substance, conventionally used for external film coating of tablets, can be applied to the tablet core or cores. The film substance is applied after precompression for example.

The same substances found in the known "external film coating" of tablets, possibly in a higher concentration may be used. To apply the film or films, a high-pressure spray device with a computer-controlled proportional valve can be used. The same computer-controlled piezoeletic proportional valves used for metering tablet cores can be used as proportional valves.

The "internal coating" of coated tablets proposed according to the invention has the further advantage that tablet cores spaced apart from one another an be film-coated with different substances. The substances of the individual films can have certain different disintegration properties and/or different encapsulated active substances and/or different formulations. As a result, retard forms are obtained that offer different disintegration times in a single dose for example. Of course the coated tablets produced by the method according to the invention can be "externally film-coated" in addition or exclusively.

The method according to the invention also makes it possible to make very large tablets which, have no hydrophobic lubricant inside the tablets that retards dissolution, and thus dissolve faster than conventional tablets of the same size. This smaller added amount of lubricant is achieved by the application, known of itself, of the lubricant to the walls of the compression chamber in contrast to the known direct admixture of the lubricant with the tablet material. As a result, the generation of $CO_2$ that is required in conventional effervescent tablets to increase the dissolution rate can be eliminated.

The $CO_2$ that is produced here for example by at least two tablet cores, one of which consists of a conventional hydrogen carbonate and the other of a conventional acid, can be used as an indicator for the complete dissolution of the coating which in this case contains active substances, flavorants, and other additives or is used to improve the taste.

The additive for example is an adhesive gel former that prevents the $CO_2$-forming substance from floating as a result of the gas formation that occurs during activation.

It should be made expressly clear that the term "tablet" used above is not limited to tablets in the pharmaceutical area alone. This term within this application also subsumes "bonbons" or other "tablet-like" objects. In the food area, pasty cores of chocolate or cocoa butter are possible for example. The cores can also contain freeze-dried pieces of fruit and/or pastes. Cores are also possible that consist of several different layers.

What is claimed is:

1. Method for manufacturing coated tablets from tablet cores and coating granulate using a press that has at least one compression chamber, and a feed device for tablet cores, comprising:

adding at least one pasty tablet core to the coating granulate to be compressed, and compressing the coating granulate and the tablet cores simultaneously in a single pressing step.

2. Method according to claim 1, wherein at least two tablet cores separate from one another are added to the coating granulate.

3. Method according to claim 1, wherein the consistency and the viscosity of the pasty tablet core mass are such as to inject the tablet core mass into the coating granulate by means of high pressure feeding means .

4. Method according to claim 3, wherein a proportional valve is used for metering the tablet core mass added by the high pressure feeding means.

5. Method according to claim 4, wherein the cross section and the throughput volume of the proportional valve are adjustable by computer controlled piezoelectric means.

6. Method according to claim 1, wherein the compression chamber is initially partially filled with coating granulate, then after the at least one pasty tablet core is added, additional coating granulate is added to the compression chamber to completely fill the compression chamber.

7. Method for manufacturing coated tablets from tablet cores and coating granulate by means of a press with at least one compression chamber and a feed device for tablet cores, comprising:

(a) adding the coating granulate to compression chamber;

(b) precompressing the coating granulate in the compression chamber;

(c) after step (b), adding a pasty tablet core to the core to the compression chamber; and (d) compressing the coating granulate simultaneously with the tablet core.

8. Method according to claim 7, wherein a film substance is applied to the tablet core after precompression.

9. Method according to claim 8, wherein tablet cores spaced apart from one another are film-coated with different substances.

10. Method according to claim 9, wherein the different substances differ in terms of their disintegration time.

11. Method according to claim 8, wherein high-pressure high-pressure feeding means with a computer-controlled proportional valve is used for applying the film substance.

12. Method according to claims 11, wherein a computer-controlled piezoelectric proportional valve is used as the valve that operates in proportion to the control and whose throughput volume and cross section are adjustable.

13. Use of the method according to claim 1 to produce effervescent tablets which have at least two tablet cores, with one containing a hydrogen carbonate and another containing an acid.

14. A method for manufacturing coated tablets, comprising:

(a) adding at least one pasty tablet core to a coating granulate;

(b) simultaneously compressing the at least one pasty tablet core and the coating granulate within a compression chamber of a press such that the at least one pasty tablet core and the coating granulate are compressed in a single pressing step; and (c) forming tablets in which material of the coating granulate surrounds material of the at least one pasty tablet core.

15. A method according to claim 14, wherein at least two pasty tablet cores, separated from another, are add ed to the coating granulate.

16. A method of according to claim 14, wherein the at least one tablet core is added to the coating granulate in step (a) by injecting the at least one pasty tablet core from a high pressure feeder.

17. A method according to claim wherein 14, both a hydrogen carbonate pasty tablet core and an acid pasty tablet core are added to the coating granulate, the pasty tablet cores being added separately to prevent chemical and physical reaction therebetween.

18. A method for manufacturing coated tablets, comprising:

(a) adding coating granulate to a compression chamber of a press;

(b) precompressing the coating granulate;

(c) after step (b), adding at least one pasty tablet core to the coating granulate; and (d) compressing the coating granulate together with the at least one pasty tablet core to form tablets in which material of the coating granulate surrounds material of the at least one pasty tablet core.

19. A method according to claim 18, wherein at least two pasty tablet cores, separated from another, are added to the coating granulate.

20. A method of according to claim 18, wherein the at least one pasty tablet core is added to the coating granulate in step (c) by injecting the at least one pasty tablet core from a high pressure feeder.

21. A method according to claim 18, wherein both a hydrogen carbonate pasty tablet core and an acid pasty tablet core are added to the coating granulate, the pasty tablet cores being added separately to prevent chemical and physical reaction therebetween.

* * * * *